United States Patent
Hu et al.

(10) Patent No.: US 10,821,219 B2
(45) Date of Patent: Nov. 3, 2020

(54) COLD AND HEAT EXCHANGE SYSTEM FOR CARDIAC SURGICAL OPERATION WITH CARDIAC ARREST

(71) Applicants: Weiwen Hu, Tianjin (CN); Ulrich Blumendeller, Dinnington (GB)

(72) Inventors: Weiwen Hu, Tianjin (CN); Ulrich Blumendeller, Dinnington (GB)

( * ) Notice: Subject to any disclaimer, the term of this patent is extended or adjusted under 35 U.S.C. 154(b) by 150 days.

(21) Appl. No.: 16/308,057

(22) PCT Filed: Aug. 17, 2016

(86) PCT No.: PCT/CN2016/095632
§ 371 (c)(1),
(2) Date: Dec. 7, 2018

(87) PCT Pub. No.: WO2018/018673
PCT Pub. Date: Feb. 1, 2018

(65) Prior Publication Data
US 2019/0307942 A1 Oct. 10, 2019

(30) Foreign Application Priority Data
Jul. 29, 2016 (CN) .......................... 2016 1 0627405

(51) Int. Cl.
*A61M 1/36* (2006.01)
*F04B 43/12* (2006.01)
(Continued)

(52) U.S. Cl.
CPC ........... *A61M 1/369* (2013.01); *A61F 7/0097* (2013.01); *A61M 1/1698* (2013.01); *A61M 1/36* (2013.01);
(Continued)

(58) Field of Classification Search
CPC ...... A61M 1/369; A61M 1/1698; A61M 1/36; A61M 1/3664; A61M 1/3666; A61M 2007/0054; A61M 2205/11; A61M 2205/3368; A61M 2205/3606; A61M 2205/3626; A61M 2205/366; A61F 7/0097; F04B 41/12; F04B 41/1292
See application file for complete search history.

(56) References Cited

U.S. PATENT DOCUMENTS

6,156,007 A * 12/2000 Ash ..................... A61M 1/3679
604/113
7,806,915 B2 * 10/2010 Scott ..................... A61M 1/369
607/106
(Continued)

*Primary Examiner* — Philip R Wiest
(74) *Attorney, Agent, or Firm* — Enshan Hong; VLP Law Group LLP (57) ABSTRACT

A cold and heat exchange system for a cardiac surgical operation with cardiac arrest, comprising: an ice water tank (15), a primary circulation water tank (11), and a secondary circulation water tank (16). Side walls of the primary circulation water tank (11) and the secondary circulation water tank (16) are each provided with an overflow orifice which is connected to the ice water tank (15) through a circulation pipe (14). A first roller pump (12) is mounted on a first hose (13). A second roller pump (18) is mounted on a second hose (17). The primary circulation water tank (11) is mounted on a first loop (5) and a second loop (6). The secondary circulation water tank (16) is mounted on a third loop (1).

14 Claims, 4 Drawing Sheets

(51) Int. Cl.
*A61M 1/16* (2006.01)
*A61F 7/00* (2006.01)

(52) U.S. Cl.
CPC ........ *A61M 1/3664* (2013.01); *A61M 1/3666* (2013.01); *F04B 43/12* (2013.01); *F04B 43/1292* (2013.01); *A61F 2007/0054* (2013.01); *A61M 2205/11* (2013.01); *A61M 2205/3368* (2013.01); *A61M 2205/3606* (2013.01); *A61M 2205/366* (2013.01); *A61M 2205/3626* (2013.01)

(56) References Cited

U.S. PATENT DOCUMENTS

| | | |
|---|---|---|
| 9,375,345 B2 * | 6/2016 | Levinson .................. A61F 7/10 |
| 10,675,176 B1 * | 6/2020 | Coakley ................ A61F 7/0085 |
| 2012/0029408 A1 * | 2/2012 | Beaudin ................ A61M 1/369 |
| | | 604/4.01 |
| 2019/0175813 A1 * | 6/2019 | Spearman ........... A61M 1/3607 |
| 2019/0192748 A1 * | 6/2019 | Berch ....................... A61L 9/16 |
| 2019/0209762 A1 * | 7/2019 | Turner ................ A61M 1/1698 |
| 2020/0179587 A1 * | 6/2020 | Spearman ........... A61M 1/3496 |

* cited by examiner

COLD AND HEAT EXCHANGE SYSTEM FOR CARDIAC SURGICAL OPERATION WITH CARDIAC ARREST

RELATED APPLICATIONS

This is a U.S. national stage of international application No. PCT/CN2016/095632 filed on Aug. 17, 2016, which claims priority from China Patent Application No. 201610627405.7 filed on Jul. 29, 2016, the entire content of which is incorporated herein as reference.

TECHNICAL FIELD

The present disclosure belongs to the field of medical devices, and particularly to a cold and heat exchange system for a cardiac surgical operation with cardiac arrest.

BACKGROUND

In a cardiac surgical operation with cardiac arrest, it is required to carry out extracorporeal blood circulation because a heart is in a stop state and blood circulation and oxygenation in a human body must continue. At present, an artificial heart-lung machine system is widely applied to clinic. The artificial heart-lung machine system includes a group of blood pumps, a cold and heat exchange water tank and a monitor and so on plus disposal articles such as an oxygenator and tubes, where the blood pumps are used to provide power to drive blood in a human body to circulate in a closed loop connected in series with an oxygenator.

Since relative differences exist between artificial blood circulation and natural blood circulation, if an operation takes a long time, these differences may cause damage to organs of a human, especially to brain tissues due to shortage of oxygen. To reduce these damages, it is required to reduce a metabolism level of a human body to lower demand of the human body for oxygen, thereby protecting human organs relatively. In a cardiac surgical operation with cardiac arrest, the cold and heat exchange water tank provides cold water or hot water to a closed-loop circuit of the oxygenator, and the cold water or hot water performs cold and heat exchange with a blood circuit in the oxygenator (the water circuit and the blood circuit in the oxygenator are isolated and perform heat exchange through an isolation interface.). Blood is cooled by cold water at the start of an operation and heated by hot water at the end of the operation. The monitor collects different human signs of a patient under operation and other important data in an extracorporeal circulation to ensure normal circulation. Thus, one extracorporeal circulation process is basically constituted.

Figure 7:
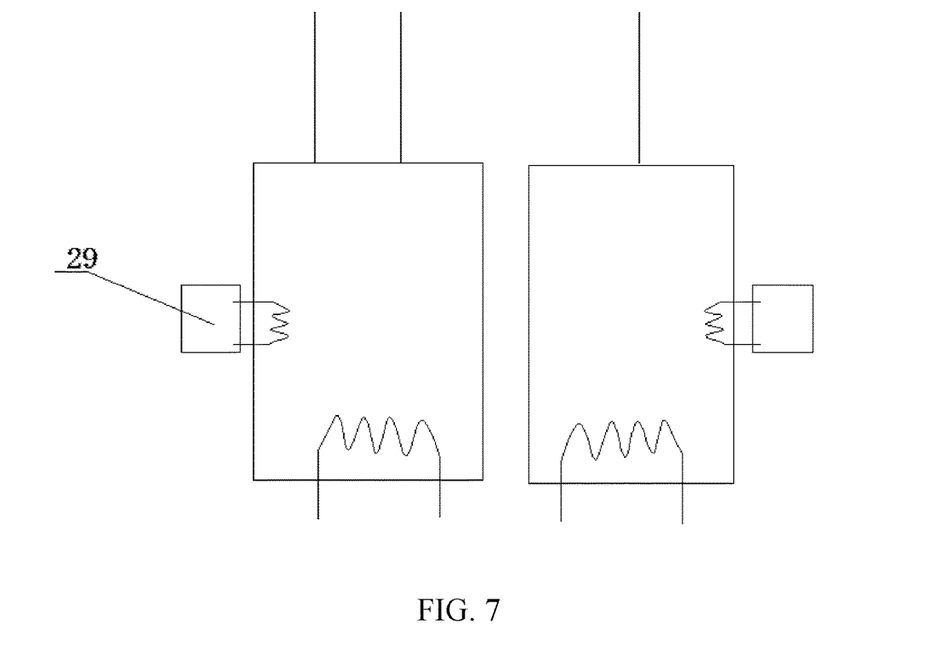
FIG. 7 is a schematic diagram illustrating a structure of a cold and heat exchange water tank for a cardiac surgical operation with cardiac arrest in the prior art.

At present, a cold and heat exchange water tank mostly applied in the world is a water tank from a particular Germany brand. The water tank includes two water sinks, a compressor, an electric heating tube and a control circuit, where the two water sinks are denoted by a water sink a and a water sink b respectively. As shown in FIG. 7, each of the water sink a and the water sink b is provided with a compressor 29 and an electric heating tube. A refrigeration tube of the compressor is maintained in a refrigeration state to allow the water sink a and the water sink b to reach a desired water temperature by controlling the working time of the electric heating tube. The water sink a provides two output water circuits of the same water temperature, that is, a first circuit and a second circuit; the water sink b provides a third circuit, and a water temperature of the third circuit is different from the water temperature of the first circuit and the second circuit. Therefore, the water tank has three circuits that can output water of two different water temperatures.

The first circuit is connected in series with an oxygenator, the second circuit is connected in series with a temperature-variable blanket and the third circuit is a cardioplegic solution circuit, where the first circuit performs cold and heat exchange with the blood circuit in the oxygenator through the output cold water or hot water to decrease or increase a blood temperature of a patient during an operation; the second circuit assists the patient to increase or decrease his body temperature through the temperature-variable blanket; and the third circuit is used to lower the heart temperature of the patient to protect his cardiac muscles.

However, a regulatory authority of Switzerland firstly finds (confirmed by EU and regulatory authorities of different countries later) that a potential hazard exists in the heat exchange water tanks that are used in the world at present. Because one heat exchange water tank may be used cyclically in an operation room and some water may remain in the heat exchange water tank after one operation is completed, the remaining water may breed a large number of pathogenic bacteria; in addition, a water pump used for driving the heat exchange water tank to output water may also produce bacteria due to contact with water. Most importantly, the produced bacteria may be dispersed into air by fans of the water pump and the compressor during a water circulation process and then enter the opened chest of the patient.

At present, there is a report confirming the above viewpoint. It is reported that (S Haller, et al. CONTAMINATION DURING PRODUCTION OF HEATER-COOLER UNITS BY MYCOBACTERIUM CHIMAERA POTENTIAL CAUSE FOR INVASIVE CARDIOVASCULAR INFECTIONS: RESULTS OF AN OUTBREAK INVESTIGATION IN GERMANY, APRIL 2015 TO FEBRUARY 2016, Eurosurveillance, Volume 21, Issue 17, 28 Apr. 2016) a plurality of patients who suffer from infections have ever used the same heat exchange water tank from a Germany manufacturer in a cardiac surgical operation with cardiac arrest. An article (Public Health England, publication gate number is 2015394) publicly reported that "a cold and heat exchange water tank may produce vapor containing bacteria during processes of extracorporeal circulation and ECMO (extracorporeal membrane oxygenation) and cause the patients to be infected". Also, the article implied that the infectious bacteria are tubercle *bacillus*. In addition, a literature reported that (Gotting T, Klassen S, Jonas D, et al. Heater-cooler units: contamination of crucial devices in cardiothoracic surgery.[J]. Journal of Hospital Infection, 2016.) a plurality of serious infections with Mycobacterium chimaera were found, and these patients were infected several months or several years after receiving thoracotomy.

In view of the above findings, manufacturers of the cold and heat exchange water tank put forward different methods of killing bacteria, such as ultraviolet sterilization, drug sterilization and filtered water. Although the bacteria quantity can be reduced immediately after the ultraviolet sterilization, drug sterilization and filtered water are adopted, the bacteria quantity may restore to a level before sterilization after a given period, and the bacteria have a given quantity of antibodies at this time. Thus, the methods of killing bacteria cannot solve the problem thoroughly.

A root cause for producing bacteria in the cold and heat exchange water tank lies in water, and any articles will produce bacteria in a water environment after contacting with water. Thus, a key to solve the problems is to transform all parts contacting with water during work into disposable articles. However, water sinks of a conventional cold and heat exchange water tank are fixedly mounted with compressors and the refrigeration tubes of the compressors perform refrigeration by reaching into the water sinks. If the cold and heat exchange water tank is replaced as a disposable article together with compressors after each operation, a huge amount of costs will be caused. Thus, a large-scale application cannot be carried out. Further, it is required to add fluorine if the refrigeration tubes are cut to separate from the compressors, leading to infeasibility in reality.

To solve the above problems, we have ever adopted vaporization refrigeration of liquid carbon dioxide, refrigeration of liquid nitrogen and refrigeration of dry ice as a replacement of the compressor to improve applicability of the cold and heat exchange water tank serving as a disposable article. But the result is not satisfactory. The vaporization refrigeration of liquid carbon dioxide requires a liquid carbon dioxide cylinder as a carrier. During an operation, it is desired to place the liquid carbon dioxide cylinder in an operation room, which may easily cause dangers as well as a large amount of cylinder replacement work. In addition to this, vaporized carbon dioxide has an extremely low efficiency in lowering water temperature because the liquid carbon dioxide is already vaporized at the outlet of the cylinder. In spite of high refrigeration efficiency of the liquid nitrogen, the storage and operation of the liquid nitrogen are very difficult and frost bites are easily caused during the operation. The dry ice does not only have a problem of high costs but also is difficult to transport and store. During storage, the dry ice may produce a large quantity of carbon dioxide gas due to increase of temperature, and a storage container will suffer from increasing pressure, easily resulting in dangers such as explosion.

Therefore, the above methods cannot solve the problems thoroughly.

SUMMARY

To overcome the defects of the prior art, the present disclosure provides a cold and heat exchange system for a cardiac surgical operation with cardiac arrest. The cold and heat exchange system is provided with an ice water sink, a main circulating water sink and an auxiliary circulating water sink, all of which serve as disposable articles, thereby eliminating the possibility of production of bacteria thoroughly.

The objects of the present disclosure are implemented based on the following technical solutions.

A cold and heat exchange system for a cardiac surgical operation with cardiac arrest includes an ice water sink, a first hose, a second hose, two flow-through tubes, a main circulating water sink and an auxiliary circulating water sink, where the main circulating water sink and the auxiliary circulating water sink are respectively mounted with one heating device; one overflow orifice is respectively formed on side walls of the main circulating water sink and the auxiliary circulating water sink, and each overflow orifice is connected to the ice water sink through one flow-through tube for overflowing water exceeding a height of the overflow orifice back to the ice water sink; the first hose is provided with a first roller pump and the second hose is provided with a second roller pump, and the water in the ice water sink is pumped respectively into the main circulating water sink and the auxiliary circulating water sink through the first hose and the second rose.

The main circulating water sink is mounted on a first circuit and a second circuit respectively. The first circuit is provided with a first circuit pump so that water in the first circuit may perform cold and heat exchange with blood in an oxygenator; the second circuit is provided with a second circuit pump so that water in the second circuit may perform cold and heat exchange with a temperature-variable blanket; the auxiliary circulating water sink is provided on a third circuit, and the third circuit is provided with a third circuit pump so that water in the third circuit may perform cold and heat exchange with blood in a cardioplegic solution circuit.

In above technical solution, the heating device is an electric heater.

An electric control system is included in the above technical solution. The electric control system may include a programmable controller, a first electric motor for driving the first roller pump, a second electric motor for driving the second roller pump, a first circulation motor for driving the first circuit pump and a second circulation motor for driving the second circuit pump, a third circulation motor for driving the third circuit pump, a temperature sensor, an amplifier and a human-machine interface. The human-machine interface is electrically connected with the programmable controller; the main circulating water sink and the auxiliary circulating water sink are internally provided with the temperature sensor respectively, each of the temperature sensors is electrically connected with one of the amplifiers and each of the amplifiers is electrically connected with the programmable controller; the first electric motor and the second electric motor are electrically connected with the programmable controller respectively; each of the electric heaters is electrically connected with the programmable controller.

In the above technical solution, one port of each of the first hose and the second hose protrudes into the ice water sink from an upper end surface of the ice water sink.

In the above technical solution, the other ports of the first hose and the second hose protrude in from upper end surfaces of the main circulating water sink and the auxiliary circulating water sink respectively.

In the above technical solution, the first circuit pump, the second circuit pump and the third circuit pump all are roller pumps.

In the above technical solution, the roller pump is a dual circuit roller pump. The dual circuit roller pump includes a pump body, a rotating wheel, a main shaft and a roller. A hollow cavity is formed in the pump body. One end of the main shaft penetrates into the cavity from a central position of a bottom surface of the cavity and is assembled with the rotating wheel in the cavity; one opening is formed respectively at positions that are on side walls of the cavity and radially opposite to each other, and two circuit hoses penetrate into the cavity from one opening and protrude out from the other opening respectively along two sides of the rotating wheel; the rotating wheel is provided with a plurality of rollers and each of the two circuit hoses is squeezed by at least one roller at any time point; the two circuit hoses are a tube before a corresponding circuit performs cold and heat exchange and a tube after cold and heat exchange is performed respectively.

In the above technical solution, the rollers are uniformly mounted on the rotating wheel along a circumferential direction with the main shaft as a center.

In the above technical solution, the number of the rollers ranges from 3 to 9.

In the above technical solution, the number of the rollers is 3.

In the above technical solution, a minimum distance of the roller from the inner side wall of the cavity is less than or equal to two times the wall thickness of the circuit hose.

In the above technical solution, the cavity is of cylindrical shape or elliptical cylindrical shape.

In the above technical solution, the circuit hose is a silicon plastic tube or a silicon tube.

In the above technical solution, two ends of any one of the circuit hoses are provided with tube clips for fixing a position of the circuit hose in the cavity.

In the above technical solution, a support plate is provided respectively at two openings of the pump body, and the tube clip is mounted on the support plate.

In the above technical solution, the pump body is hinged with a pump cover.

Compared with the prior art, the cold and heat exchange system of the present disclosure has the following benefits:

1. A conventional cold and heat exchange water tank serving as a refrigerating device (compressor) is transformed into an ice water sink (refrigerate with ice blocks) with high safety and low cost of refrigeration source so that all parts of the ice water sink, the main circulating water sink, the auxiliary circulating water sink and tubes of the first to three circuits that contact with water all become disposable articles, thereby eliminating possibility of production of bacteria thoroughly.

2. In the present disclosure, the first circuit pump, the second circuit pump and the third pump are all preferably dual circuit roller pumps. When a rotating wheel of a dual circuit roller pump rotates, one circuit hose outputs liquid from the main circulating water sink/the auxiliary circulating water sink and the other circuit hose inputs liquid at the same flow rate into the main circulating water sink/the auxiliary circulating water sink so that a water level of the main circulating water sink/the auxiliary circulating water sink remains constant.

3. In the prior art, the first circuit pump is a water pump. Water in the first circuit is pumped into a cold and heat exchanger of an oxygenator by the water pump and performs cold and heat exchange with blood in the oxygenator so that a given pressure exists in the cold and heat exchanger and excessive pressure may cause the blood and the water to be fused or cause damage to the cold and heat exchanger. In the cold and heat exchange system of the present disclosure, after a dual circuit roller pump is adopted, one circuit hose applies a pressure to the cold and heat exchanger and the other circuit hose forms a negative pressure on the cold and heat exchanger. The two pressures are counteracted mutually, thereby solving a problem of fusion of blood and water or damage to the cold and heat exchanger caused by excessive pressure.

4. In the prior art, the third circuit and the cardioplegic solution circuit both are connected with an airtight container with a complex structure to realize cold and heat exchange (a special structure is arranged in the container to separate blood and water) and the airtightness is used to apply a pressure to allow the container to perform water circulation through the third circuit. In the technical solution of the present disclosure, after a dual circuit roller pump is adopted, since the dual circuit roller pump has an effect of keeping a water level constant (see benefit 2), cold and heat exchange can be performed only by directly putting the tube of the cardioplegic solution circuit into an open container with a simple structure, without need to perform connection operation for cardioplegic solution circuit and therefore the dual circuit roller pump features convenient operation, simple structure and low costs.

In the drawings, 1 is a third circuit, 2 is a container, 3 is a temperature-variable blanket, 4 is an oxygenator, 5 is a first circuit, 6 is a second circuit, 7 is a first circuit pump, 8 is a second circuit pump, 9 is a temperature sensor, 10 is an electric heater, 11 is a main circulating water sink, 12 is a first roller pump, 13 is a first hose, 14 is a flow-through tube, 15 is an ice water sink, 16 is an auxiliary circulating water sink, 17 is a second hose, 18 is a second roller pump, 19 is a third circuit pump, 20 is an amplifier, 21 is a human-machine interface, 22 is a programmable controller, 23 is a third circulation motor, 24 is a motor driver, 25 is a first circulation motor, 26 is a second circulation motor, 27 is a first electric motor, 28 is a second electric motor, 29 is a compressor, 30 is an opening, 31 is a rotating wheel, 32 is a main shaft, 33 is a pump body, 34 is a circuit hose, 35 is a tube clip, 36 is a support plate, 37 is a roller and 38 is a bearing.

DETAILED DESCRIPTION OF PREFERRED EMBODIMENTS

The cold and heat exchange system for a cardiac surgical operation with cardiac arrest in the present disclosure will be detailed below in combination with the accompanying drawings.

As shown in the FIGS. 1-6, an ice water tank 15 for receiving a mixture of water and ice from an ice making device (not shown), a first hose 13, a second hose 17, two flow-through tubes 14, an electric control system, a main circulating water sink 11, an auxiliary circulating water sink 16 are included, where the main circulating water sink 11 and the auxiliary circulating water sink 16 are provided with an electric heater 10 respectively and the electric heater 10 has a power of 2400 W. An overflow orifice (not shown) is formed respectively on side walls of the main circulating water sink 11 and the auxiliary circulating water sink 16, and each overflow orifice is connected with the ice water sink 15 through one flow-through tube 14 for overflowing water exceeding a height of the overflow orifice back to the ice water sink 15. The first hose 13 is provided with a first roller pump 12 and the second hose 17 is provided with a second roller pump 18. Water in the ice water sink 15 is pumped into the main circulating water sink 11 and the auxiliary circulating water sink 16 through the first hose 13 and the second hose 17 respectively. One port of each of the first hose 13 and the second hose 17 protrudes into the ice water sink 15 from an upper end surface of the ice water sink 15, and the other port of the first hose 13 protrudes into the main circulating water sink 11 from an upper end surface of the main circulating water sink 11 and the other port of the second hose 17 protrudes into the auxiliary circulating water sink 16 from an upper end surface of the auxiliary circulating water sink 16.

Figure 1:
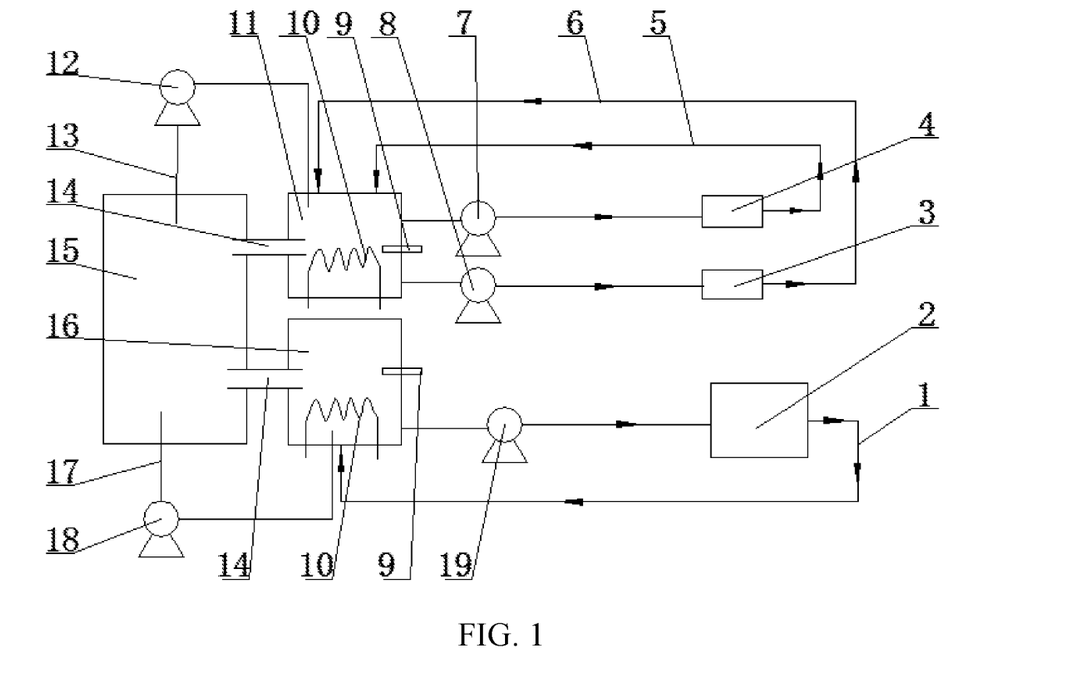
FIG. 1 is a schematic diagram illustrating a structure of a cold and heat exchange system for a cardiac surgical operation with cardiac arrest according to an example of the present disclosure.
Figure 2:
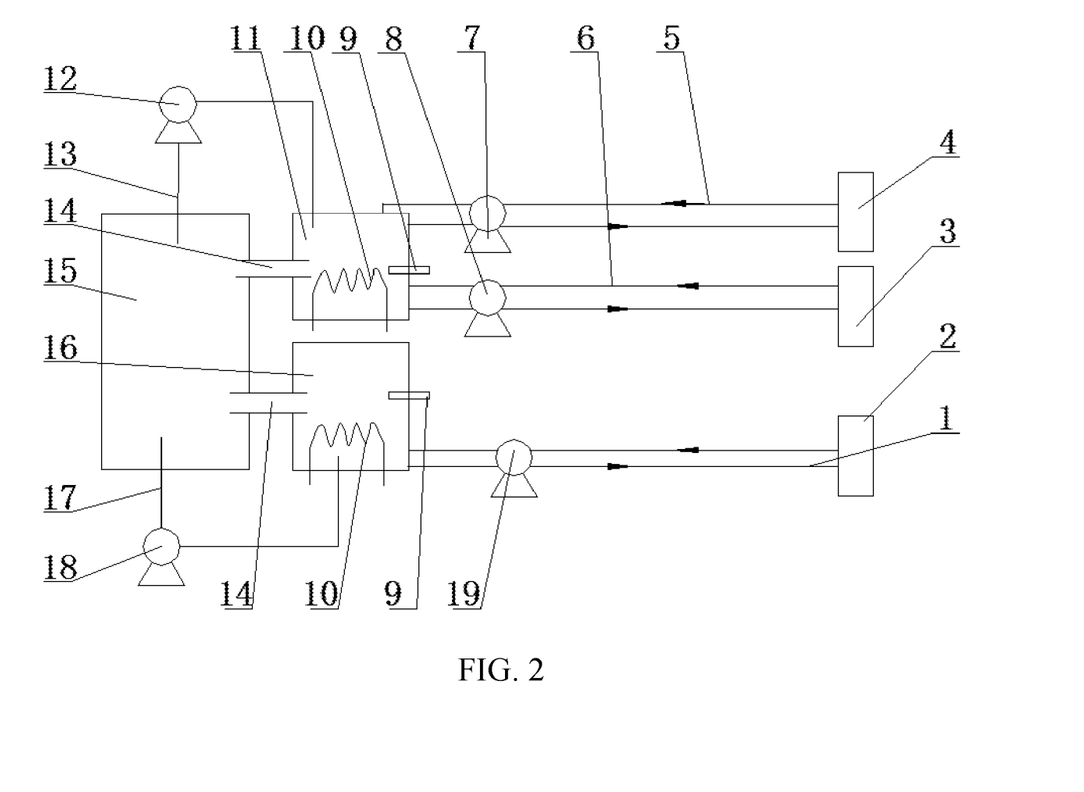
FIG. 2 is a schematic diagram illustrating a structure of a cold and heat exchange system for a cardiac surgical operation with cardiac arrest according to another example of the present disclosure.
Figure 3:
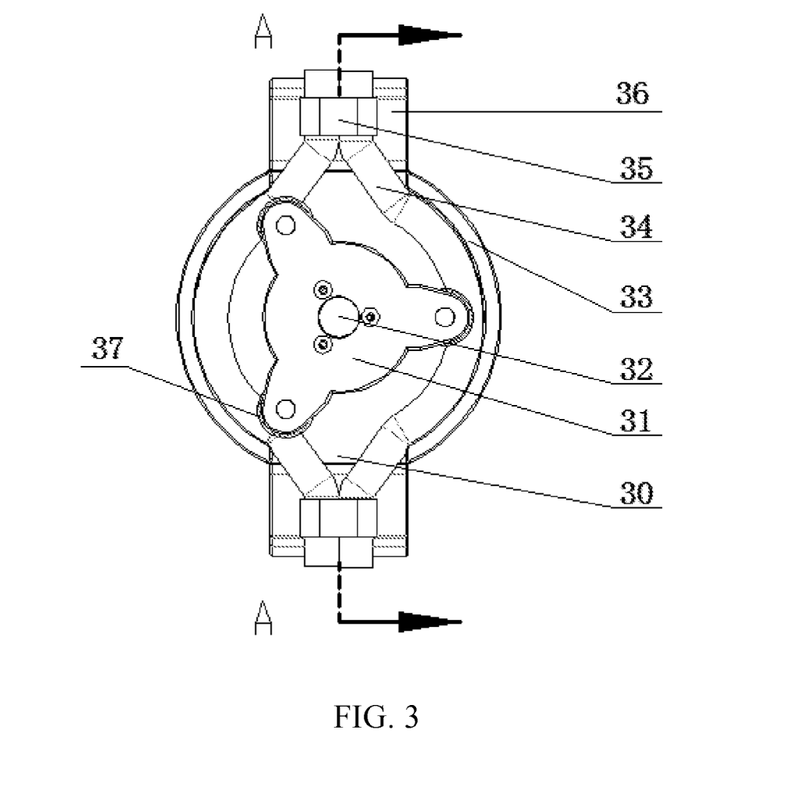
FIG. 3 is a top view of a dual circuit roller pump according to an example of the present disclosure.
Figure 4:
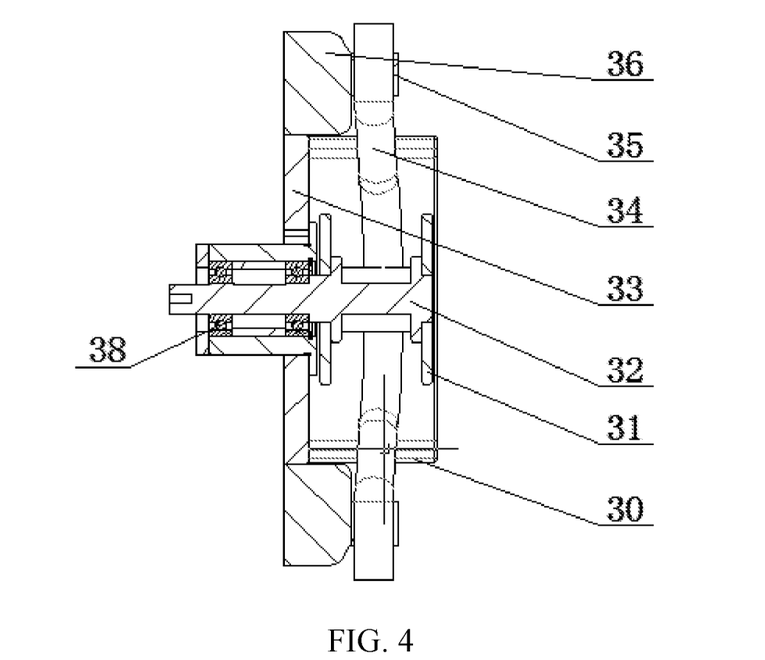
FIG. 4 is sectional view of the dual circuit roller pump taken along A-A line in FIG. 3.
Figure 5:
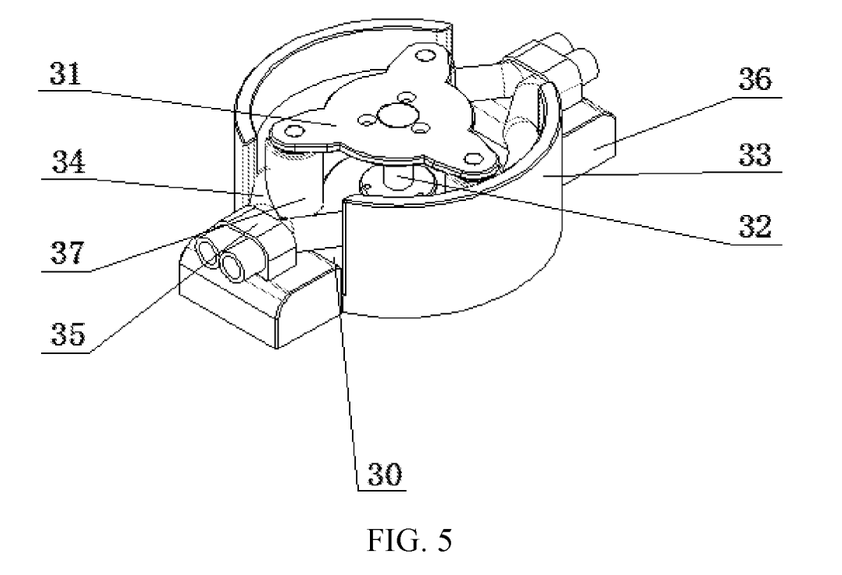
FIG. 5 is a schematic diagram illustrating a stereoscopic structure of a dual circuit roller pump according to an example of the present disclosure.

The main circulating water sink 11 is mounted on a first circuit 5 and a second circuit 6 respectively (the main circulating water sink 11 is respectively communicated with the first circuit 5 and the second circuit 6.). A first circuit pump 7 is provided on the first circuit 5 so that water in the first circuit 5 may perform cold and heat exchange with blood in an oxygenator 4 to decrease or increase a blood temperature of a patient during a cardiac surgical operation with cardiac arrest; a second circuit pump 8 is provided on the second circuit 6 so that water in the second circuit 6 may perform cold and heat exchange with a temperature-variable blanket 3 to assist the patient to decrease or increase his body temperature through the temperature-variable blanket 3. The auxiliary circulating water sink 16 is provided on a third circuit 1 (the auxiliary circulating water sink 16 is in communication with the third circuit 1.) and a third circuit pump 19 is provided on the third circuit 1 so that water in the third circuit 1 may perform cold and heat exchange with blood in a cardioplegic solution circuit to reduce a heart temperature of a patient under operation and protect his cardiac muscles; the third circuit is in communication with a container 2, and water in the third circuit flows through the container 2 and performs cold and heat exchange with blood in the cardioplegic solution circuit in the container 2.

In the technical solution, the first circuit pump 7, the second circuit pump 8 and the third circuit pump 19 are preferably roller pumps, and more preferably are dual circuit roller pumps as shown in FIG. 2. The dual circuit roller pump includes: a pump body 33 hinged with a pump cover, a rotating wheel 31, a main shaft 32, and a roller 37. A hollow cavity of a cylindrical shape or an elliptical cylindrical shape is formed in the pump body 33, and one end of the main shaft 32 penetrates into the cavity form a central position of a bottom surface of the cavity and is assembled with the rotating wheel 31 in the cavity. Two bearings 38 are mounted between the main shaft 32 and the pump body 33. An opening 30 is formed respectively at positions that are on the side wall of the cavity and radially opposite to each other. Two circuit hoses 34 (the two circuit hoses 34 are a tube before a corresponding circuit performs cold and heat exchange and a tube after cold and heat exchange is performed and the circuit hoses 34 are silicon plastic tubes or silicon tubes.) both penetrate into the cavity from one opening 30 and protrude out from the other opening 30 respectively along two sides of the rotating wheel 31; the rotating wheel 31 is mounted with three rollers 37 and the three rollers 37 are uniformly mounted on the rotating wheel 31 along a circumferential direction with the main shaft 32 as a center so that each of the two circuit hoses 34 can be squeezed by at least one roller 37 at any time point. A minimum distance of the roller 37 from the inner side wall of the cavity is less than or equal to two times the wall thickness of the circuit hose 34. Two ends of any one of the circuit hoses 34 are provided with tube clips 35. The tube clip 34 is mounted on a support plate 36 provided at each opening 30 to fix a position of the circuit hose 34 in the cavity.

Figure 6:
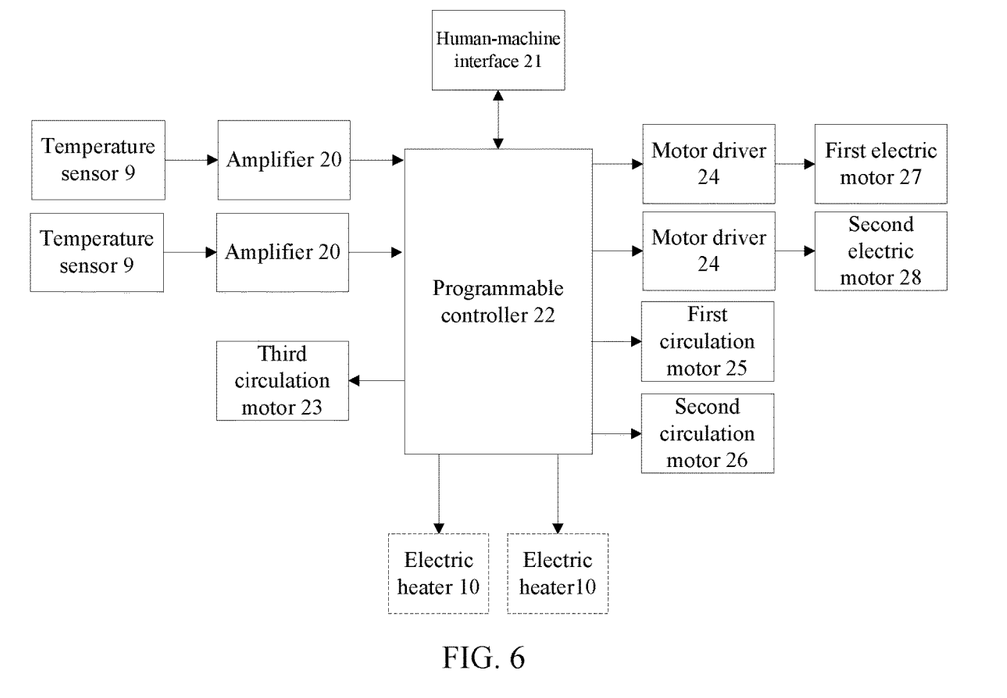
FIG. 6 is a schematic diagram illustrating an electric control system of a cold and heat exchange system for a cardiac surgical operation with cardiac arrest according to an example of the present disclosure.

An electric control system includes a programmable controller 22 (may be PLC), a first electric motor 27 for driving the first roller pump 12, a second electric motor 28 for driving the second roller pump 18, a first circulation motor 25 for driving the first circuit pump 7, a second circulation motor 26 for driving the second circuit pump 8, a third circulation motor 23 for driving the third circuit pump 19, two temperature sensors 9, an amplifier 20, and a human-machine interface 21. The human-machine interface 21 is electrically connected with the programmable controller 22 to input data into the programmable controller 22; the main circulating water sink 11 and the auxiliary circulating water sink 16 are internally provided with one temperature sensor 9 respectively, each of the temperature sensors 9 is electrically connected with one amplifier 20 and each of the amplifiers 20 is electrically connected with the programmable controller 22. The first electric motor 27 and the second electric motor 28 are electrically connected with the programmable controller 22 respectively, and one motor driver 24 may also be provided at a circuit of the first electric motor 27 and the programmable controller 22 and a circuit of the second electric motor 28 and the programmable controller 22 respectively. Each of the electric heaters 10 is electrically connected with the programmable controller 22.

Before a cardiac surgical operation with cardiac arrest, sufficient ice and water are put into the ice water sink 15 at one time and water is put into the main circulating water sink 11 and the auxiliary circulating water sink 16 respectively. The electric control system starts to work, and a working process of the electric control system is as follows:

1. A desired temperature value A of the main circulating water sink 11 is written into the programmable controller 22 through the human-machine interface 21 and a temperature value B is obtained by collecting a temperature of water in the main circulating water sink 11 by the temperature sensor 9 installed in the main circulating water sink 11; the programmable controller 22 controls heating of the electric heater 10 mounted in the main circulating water sink 11 or calls ice water from the ice water sink 15 into the main circulating water sink 11 by comparing the desired temperature value A and the temperature value B so that the temperature of the water in the main circulating water sink 11 reaches the desired temperature value A.

2. A desired temperature value C of the auxiliary circulating water sink 16 is written into the programmable controller 22 through the human-machine interface 21, and a temperature value D is obtained by collecting a temperature of water in the auxiliary circulating water sink 16 by the temperature sensor 9 mounted in the auxiliary circulating water sink 1; the programmable controller 22 controls heating of the electric heater 10 mounted in the auxiliary circulating water sink 16 or calls ice water from the ice water sink 15 into the auxiliary circulating water sink 16 by comparing the desired temperature value C and the temperature value D so that the temperature of the water in the auxiliary circulating water sink 16 reaches the desired temperature value C.

3. According to the demands of oxygenator, the temperature-variable blanket and the cardioplegic solution circuit for cold and heat exchange, a signal may be input into the programmable controller 22 through the human-machine interface 21, and the programmable controller 22 may drive/stop the first circuit pump 7, the second circuit pump 8 and the third circuit pump 19 to achieve the purpose of cold and heat exchange for the oxygenator, the temperature-variable blanket and the cardioplegic solution circuit.

The cold and heat exchange system for a cardiac surgical operation with cardiac arrest in the present disclosure will be detailed below in combination with specific examples. When the weight of a patient is 80 KG, a purpose of lowering a metabolism level of a human body in a cardiac surgical operation with cardiac arrest can be achieved by putting 15-18 KG of ice (0° C.) and about 10 liters of water into the ice water sink 15. (Theoretically, 9.52 KG of ice is needed; considering a portion of heat may be lost due to melting of ice, the amount of ice actually required may be more than that required theoretically.). With the cold and heat exchange system, a conventional cold and heat exchange water tank serving as a refrigeration device (compressor) can be transformed into a ice water sink (i.e. refrigeration with ice blocks) so that all parts of the ice water sink, the main circulating water sink and the auxiliary water circulating sink that contact with water become disposable articles, thereby eliminating possibility of production of bacteria thoroughly.

The above illustrative descriptions are made to the present disclosure. It is noted that any simple changes, modifications, and equivalent substitutions made by those of ordinary skill in the prior art without departing from the core idea of the present disclosure shall all fall within the scope of protection of the present disclosure.

What is claimed is:

1. A cold and heat exchange system for a cardiac surgical operation with cardiac arrest, comprising: an ice water sink, a first hose, a second hose, two flow-through tubes, a main circulating water sink, and an auxiliary circulating water sink, wherein the main circulating water sink and the auxiliary circulating water sink are respectively provided with one heating device; an overflow orifice is formed respectively on side walls of the main circulating water sink and the auxiliary circulating water sink, and each overflow orifice is connected with the ice water sink through one flow-through tube for overflowing water exceeding a height of the overflow orifice back to the ice water sink; the first hose is provided with a first roller pump and the second hose is provided with a second roller pump, water in the ice water sink is pumped into the main circulating water sink and the auxiliary circulating water sink through the first hose and the second hose respectively;

the main circulating water sink is mounted on a first circuit and a second circuit respectively, and a first circuit pump is provided on the first circuit in such a way that water in the first circuit performs cold and heat exchange with blood in an oxygenator; a second circuit pump is provided on the second circuit in such a way that water in the second circuit performs cold and heat exchange with a temperature-variable blanket; the auxiliary circulating water sink is provided on a third circuit and a third circuit pump is provided on the third circuit in such a way that water in the third circuit performs cold and heat exchange with blood in a cardioplegic solution circuit.

2. The cold and heat exchange system according to claim 1, wherein the heating device is an electric heater.

3. The cold and heat exchange system according to claim 2, wherein the cold and heat exchange system also comprises an electric control system comprising: a programmable controller, a first electric motor for driving the first roller pump, a second electric motor for driving the second roller pump, a first circulation motor for driving the first circuit pump, a second circulation motor for driving the second circuit pump, a third circulation motor for driving the third circuit pump, a temperature sensor, an amplifier, and a human-machine interface, wherein the human-machine interface is electrically connected with the programmable controller; the main circulating water sink and the auxiliary circulating water sink are internally provided with one temperature sensor respectively, each of the temperature sensors is electrically connected with one amplifier and each of the amplifiers is electrically connected with the programmable controller; the first electric motor and the second electric motor are electrically connected with the programmable controller respectively, and each of the electric heaters is electrically connected with the programmable controller.

4. The cold and heat exchange system according to claim 1, wherein one port of each of the first hose and the second hose protrudes into the ice water sink from an upper end surface of the ice water sink; the other ports of the first hose and the second hose protrude in from upper end surfaces of the main circulating water sink and the auxiliary circulating water sink respectively.

5. The cold and heat exchange system according to claim 1, wherein the first circuit pump, the second circuit pump and the third circuit pump all are roller pumps.

6. The cold and heat exchange system according to claim 5, wherein the roller pump is a dual circuit roller pump comprising: a pump body, a rotating wheel, a main shaft and a roller, a hollow cavity is formed in the pump body, one end of the main shaft penetrates into the cavity from a central position of a bottom surface of the cavity and is assembled with the rotating wheel in the cavity; one opening is formed respectively at positions that are on side walls of the cavity and radially opposite to each other, and two circuit hoses penetrate into the cavity from one opening and protrude from the other opening respectively along two sides of the rotating wheel; the rotating wheel is provided with a plurality of rollers and each of the two circuit hoses is squeezed by at least one roller at any time point; the two circuit hoses are a tube before a corresponding circuit performs cold and heat exchange and a tube after cold and heat exchange is performed respectively.

7. The cold and heat exchange system according to claim 6, wherein the rollers are uniformly mounted on the rotating wheel along a circumferential direction with the main shaft as a center.

8. The cold and heat exchange system according to claim 7, wherein the number of the rollers (37) is 3 to 9.

9. The cold and heat exchange system according to claim 8, wherein a minimum distance of the roller from an inner side wall of the cavity is less than or equal to two times the wall thickness of the circuit hose.

10. The cold and heat exchange system according to claim 9, wherein the cavity is of cylindrical shape or elliptical cylindrical shape.

11. The cold and heat exchange system according to claim 10, wherein the circuit hose is a silicon plastic tube or a silicon tube.

12. The cold and heat exchange system according to claim 11, wherein two ends of any one of the circuit hoses are provided with tube clips for fixing a position of the circuit hose in the cavity.

13. The cold and heat exchange system according to claim 12, wherein a support plate is provided respectively at two openings of the pump body and the tube clip is mounted on the support plate.

14. The cold and heat exchange system according to claim 13, wherein the pump body is hinged with a pump cover.

* * * * *